US006196229B1

(12) United States Patent
Piazza

(10) Patent No.: US 6,196,229 B1
(45) Date of Patent: Mar. 6, 2001

(54) PATIENT MOBILIZER

(76) Inventor: Arlene Piazza, 38-500 Cactus La., Palm Desert, CA (US) 92260

( * ) Notice: Subject to any disclaimer, the term of this patent is extended or adjusted under 35 U.S.C. 154(b) by 0 days.

(21) Appl. No.: 09/507,013

(22) Filed: Feb. 22, 2000

(51) Int. Cl.[7] .................................................. A61B 19/00
(52) U.S. Cl. .............................. 128/869; 128/872; 5/89.1
(58) Field of Search .................................... 128/846, 845, 128/869, 870, 872–876; 5/81 P, 89.1, 81.1 HS; 2/238

(56) References Cited

U.S. PATENT DOCUMENTS

| | | | | |
|---|---|---|---|---|
| 2,560,243 | | 7/1951 | Peterson . | |
| 2,851,033 | * | 9/1958 | Posey | 128/845 |
| 3,469,268 | | 9/1969 | Phillips . | |
| 3,669,107 | * | 6/1972 | Powy | 128/845 |
| 4,159,010 | | 6/1979 | Mitro . | |
| 4,723,327 | | 2/1988 | Smith . | |
| 4,793,008 | | 12/1988 | Joansson . | |
| 4,944,057 | | 7/1990 | Shaw . | |
| 5,031,639 | * | 7/1991 | Wolfer | 128/874 |
| 5,138,731 | | 8/1992 | Harcrow, Jr. . | |
| 5,163,450 | | 11/1992 | Cadicohon et al. . | |
| 5,224,321 | * | 7/1993 | Graf | 5/81.1 HS |
| 5,442,821 | | 8/1995 | Weeks . | |
| 5,449,004 | * | 9/1995 | Sanchez | 128/846 |
| 5,570,482 | | 11/1996 | Asakawa . | |
| 5,860,114 | * | 1/1999 | Fullor | 5/81.1 HS |
| 6,101,634 | * | 8/2000 | Martinez | 128/873 |

* cited by examiner

*Primary Examiner*—Michael A. Brown
(74) *Attorney, Agent, or Firm*—Stetina Brunda Garred & Brucker; Kit M. Stetina

(57) ABSTRACT

A patient mobilizer for enabling a care giver to move a generally disabled patient. The mobilizer includes a flexible sheet for placement against the back of a patient lying face up on a supported surface, and preferably is sized to extend from an upper neck location to a lower buttock location on a patient to present a perimeter edge which is shaped to match the lateral outline of a human torso. A plurality of hand engageable handles are disposed around the perimeter of the sheet for moving, rolling, and repositioning the patient as the patient is lying down upon and secured to the sheet. Patient securement to the sheet is accomplished through a pair of releasable and length adjustable shoulder straps attached to the sheet and engageable with the respective shoulders of the patient. The shoulder straps can also be engaged with shoulders of both the patient and a care giver who is facing the patient chest to chest to thereby enable the care giver to lift and ultimately carry the patient using shoulder-directed strength.

7 Claims, 2 Drawing Sheets

PATIENT MOBILIZER

CROSS-REFERENCE TO RELATED APPLICATIONS (Not Applicable)

STATEMENT RE: FEDERALLY SPONSORED RESEARCH/DEVELOPMENT (Not Applicable)

FIELD OF THE INVENTION

The present invention relates generally to a patient mobilizing device, and more particularly to a patient mobilizer having a support sheet and strap arrangement enabling a single attendant to move and lift a disabled person situated in a lying position without additional human or mechanical assistance.

BACKGROUND OF THE INVENTION

Patient moving devices can be very helpful in providing care for disabled patients at home, especially if one individual handles the patient's basic care. Depending on the patient's disability and the relative sizes of the patient and care giver, some aspects of the patient's care such as changing clothes, moving the patient for bathing, positioning the patient for eating, and moving the patient around the home, can be physically demanding, particularly when the patient is unable to sit up without assistance. In those cases where the patient cannot sit up, he generally cannot assist his care giver with the lifting process nor position himself for movement and transport. Under these circumstances, lifting and moving the patient within the home, or even moving the patient on a bed for cleaning or changing clothes, can be a physically awkward process as the care giver attempts to leverage the weight and body position of the patient. These physical challenges can be especially problematic for those who lack the strength to safely undertake some aspects of the patient's care. For example, the care giver may carry or lift the patient in a less balanced posture, or move the patient within a bed with a series of nudges, pushes, and pulls instead of a more gentle, continuous motion. This type of handling can be potentially dangerous for both parties.

Current patient moving devices typically include a patient harness for attachment to a mechanical lifting apparatus, or a sling with hand engageable handles for manually lifting the patient. For example, Mitro (U.S. Pat. No. 4,159,010) discloses a lifting harness which can be placed around the torso of a disabled person and then attached to a separate lifting device for moving the patient. Smith (U.S. Pat. No. 4,723,327) and Weeks (U.S. Pat. No. 5,442,821) both disclose a flexible body sling with handles disposed around the perimeter of the sling for manually lifting a patient. As is apparent from these manual deigns, it would be difficult or impossible for one person to support these slings around their perimeters and thereby retain the disabled person in a stable position. Moreover, manual lifting devices generally require great arm strength to lift a patient because the sling handles are the primary means for supporting the sling and patient. For instance, Shaw (U.S. Pat. No. 4,944,057) discloses a sling which can be lifted by one person; however, the attendant must lift the patient by grasping the sling handles, the patient must be seated upright within the sling, and the patient must assist the care giver in maintaining a balanced posture by holding onto, or leaning into, the care giver.

In view of the above considerations, it is apparent that a need exists for a patient moving device which allows one person to lift and move a disabled patient without undue physical strain, hazard, or additional assistance. Consequently, one object of the present invention is to provide a patient mobilizing device that one person can readily operate for lifting a disabled patient from a prone position. Yet another object of the invention is to provide a patient mobilizing device which stabilizes the patient during transport. Another object of the invention is to provide a device for rolling and moving a patient on a supported surface as the patient is lying down. Still another object of the invention is to secure the patient to the patient mobilizing device as the patient is rolled or shifted in a lying position. These and other objects of the invention will become apparent throughout the description thereof which now follows.

SUMMARY OF THE INVENTION

The present invention is a patient mobilizer which includes a flexible sheet for placement against the back of a patient lying face up on a supported surface. The sheet is sized to extend from an upper neck location to a lower buttock location on the patient and preferably has a perimeter edge which is shaped to match the lateral contours of a human torso. The sheet also has a plurality of hand engageable handles disposed around the perimeter of the sheet for moving, rolling, and repositioning the patient as the patient is lying down on the patient mobilizer. The patient mobilizer also has a pair of releasable and length adjustable shoulder straps attached to the sheet. In one usage, the shoulder straps secure the patient to the sheet as the patient is rolled or shifted on a bed or similar supported surface. In another usage, a care giver may wrap the shoulder straps around the patient's shoulders and his own shoulders as patient and care giver face each other chest to chest, and then lift the patient using the shoulder straps and handles. As is thus evident, the shoulder straps and handles allow one person to lift the patient in a stable manner without additional mechanical or human assistance. In addition, the shoulder straps secure the patient in a stable position within the patient mobilizer as the care giver manipulates the handles for rolling and shifting the patient on a supported surface.

BRIEF DESCRIPTION OF THE DRAWINGS

An illustrative and presently preferred embodiment of the invention is shown in the accompanying drawings in which.

DETAILED DESCRIPTION OF THE PREFERRED EMBODIMENT

Figure 1:
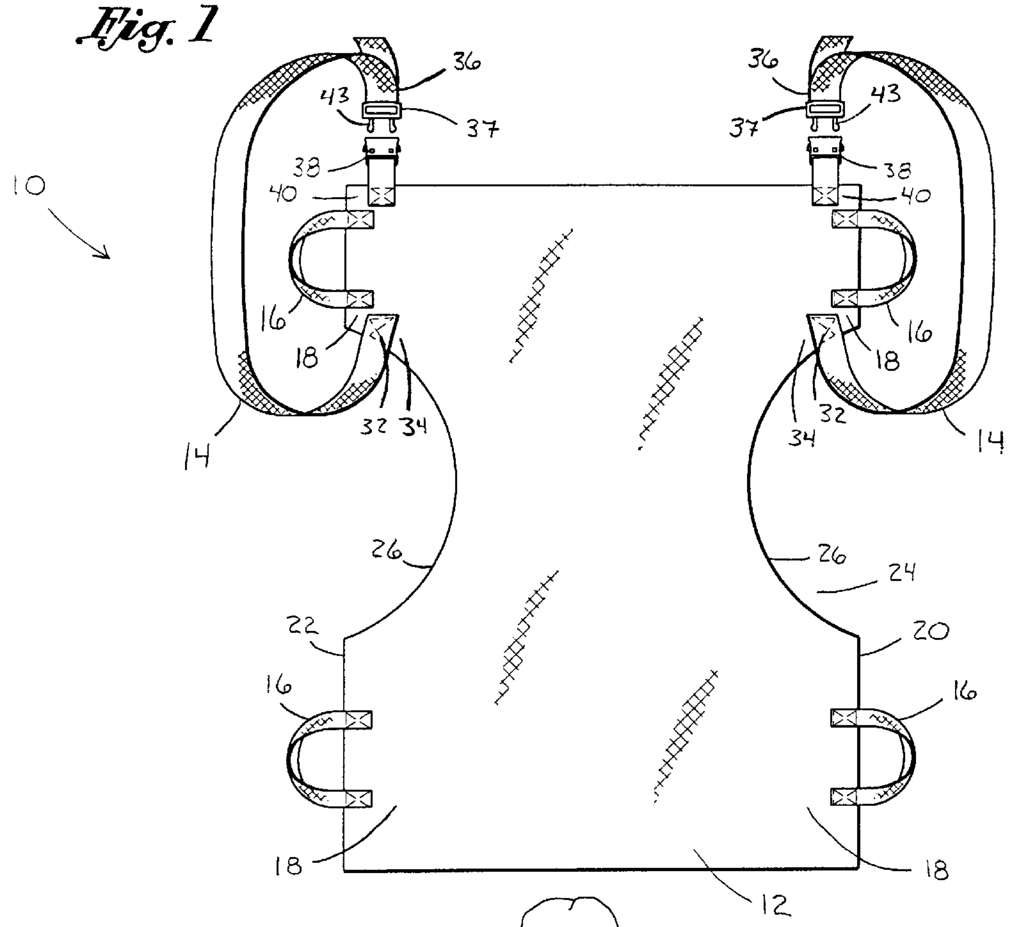
FIG. 1 is a rear perspective view of a patient mobilizer.
Figure 2:
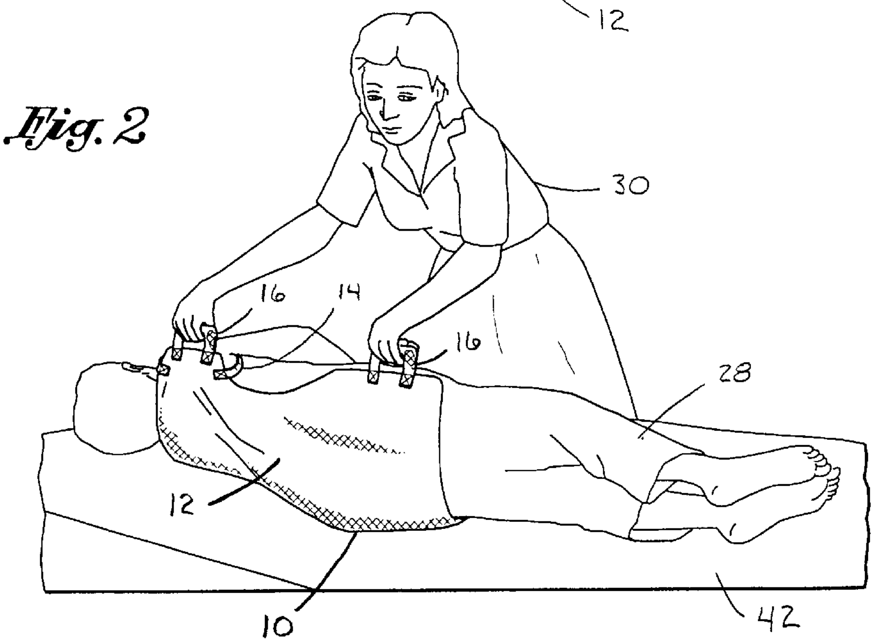
FIG. 2 is a perspective view of a patient positioned on the patient mobilizer of FIG. 1.

Referring to FIGS. 1 and 2, a patient mobilizer 10 is illustrated. The patient mobilizer 10 includes a flexible sheet 12, a pair of shoulder straps 14, and four hand engageable strap handles 16 respectively disposed on each of the four corner portions 18 of the sheet 12. In the preferred embodiment, the flexible sheet 12 is formed from a textile material, but, of course, the sheet can be constructed from any material that provides utility as here described. The sheet 12 additionally has a right side 20 and a left side 22 each having a cut to provide a cut out edge 26 for approximately matching the lateral contours of a human torso. As illustrated, the shoulder straps 14 and handles 16 are sewn to the sheet 12.

Figure 3:
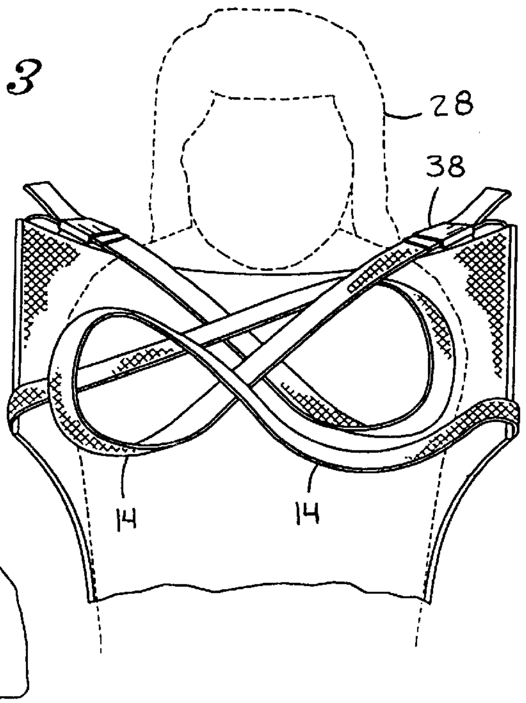
FIG. 3 is a partial front view of a patient with the patient mobilizer of FIG. 1 wrapped there about.

Referring to FIGS. 1 and 3, the shoulder straps 14 are sized for encompassing the respective shoulders of the patient 28 alone or the shoulders of both the patient 28 and care giver 30 as patient 28 and care giver 30 face each other during patient lifting. Each respective shoulder strap 14 has a first end 32 attached to a respective upper portion 34 of the sheet 12 and a second end portion 36 releasably engageable with one of the two strap engagers here shown as female snap buckles 38 attached to the top edge 40 of the flexible sheet 12. The buckles 38 receive respective conventional male plug-in spring hooks 43 attached to respective standard loops 37 through which lengths of strap 14 are manipulated to shorten or lengthen the straps 14 as shown in the art. It is, of course, recognized that other types of strap engagers may be employed, including traditional buckles having hooks for engaging holes in the shoulder straps or buckles that releasably clamp to the straps.

In operation, the patient mobilizer 12 is disposed underneath a patient 28 lying face up on a supported surface 42. From this position, the care giver 30 may pull or raise the handles 16 for shifting or rolling the patient 28 on the supported surface 42 as shown in FIG. 2. To facilitate this movement and stabilize the patient 28, the care giver 30 can fasten the patient 28 to the flexible sheet 12 by engaging and tightening the shoulder straps 14 around the patient's shoulders. For stabilizing the patient 28 within a wheel chair (not shown), the patient mobilizer 10 encompasses a seated patient with the straps 14 bridging across the chest of the patient to be wrapped behind and retained by the pusher handles of the wheel chair.

Figure 4:
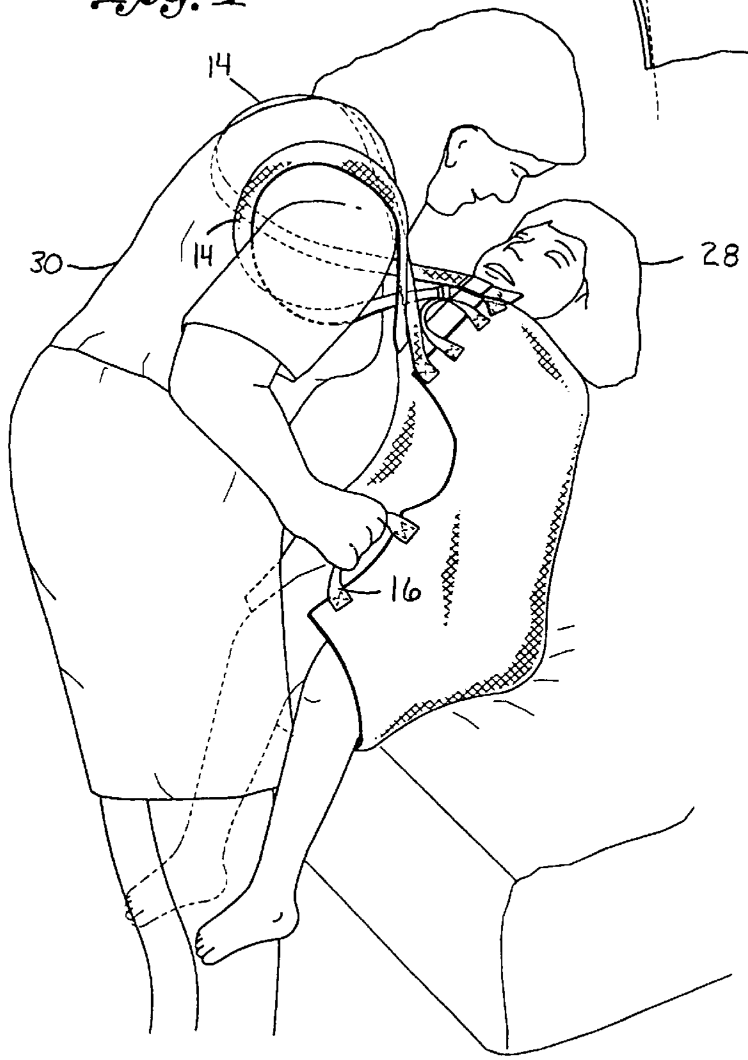
FIG. 4 is a perspective view of an attendant positioned for lifting a patient with the patient mobilizer as configured in FIG. 3.

FIGS. 3 and 4 illustrate the procedure for carrying the patient 28 over a distance. In particular, the care giver 30 first raises the patient 28 to a seated position with the patient mobilizer 10 placed against the back of the patient 28. The shoulder straps 14 are then engaged around the shoulders of the patient 28 and crisscrossed in front of the patient (FIG. 3). With this strap configuration, the care giver 30 inserts his or her arms through the loops formed by the crossed shoulder straps as the care giver 30 faces the patient 28 chest to chest as shown in FIG. 4. From this position, the care giver 30 can carry the patient 28 by grasping the two handles 16 proximate the legs of the patient 28 and lifting the patient 28 using the handles in combination with shoulder leverage. During the lifting and carrying process, the lower extremities of the patient 28 can also be positioned between the legs of the care giver 30 to promote a more balanced posture and for distributing the weight of the patient 28 more evenly across the shoulders of the care giver 30. As the patient 28 is so carried from one location to another, the patient mobilizer 10 distributes the weight of the patient 28 among the arms, shoulders, and back of the care giver 30 in such a manner that the care giver 30 may adopt a balanced and stable posture. In this manner, efficient patient mobility is achieved while requiring only one person to accomplish turning, lifting, and carrying the patient.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A patient mobilizer for placement against the back of a patient, the patient mobilizer comprising:

a) a flexible sheet having a right edge, a left edge, a top end, and a bottom end;

b) a left adjustable length shoulder strap and a right adjustable length shoulder strap each attached to the top end of the flexible sheet for engaging the respective shoulders of the patient; and c) a plurality of hand engageable handles with at least two handles disposed on the right edge of the flexible sheet on the top and bottom ends respectively, and at least two handles disposed on the left edge of the flexible sheet on the top and bottom ends respectively.

2. The patient mobilizer as claimed in claim 1 wherein the right and left shoulder straps each have a length sufficient to simultaneously encompass the respective shoulders of the patient and respective shoulders of a care giver facing the patient chest to chest.

3. The patient mobilizer as claimed in claim 1 additionally comprising shoulder strap engagers for releasably maintaining the strap in a closed configuration.

4. The patient mobilizer as claimed in claim 1 wherein a portion of each of the right edge and left edge is configured to approximate lateral curvature of a human torso.

5. The patient mobilizer as claimed in claim 4 additionally comprising shoulder strap engagers for releasably maintaining the strap in a closed configuration.

6. The patient mobilizer as claimed in claim 1 wherein the flexible sheet is sized to extend from an upper neck location to a lower buttock location of the patient.

7. The patient mobilizer as claimed in claim 1 wherein the flexible sheet is constructed from a textile material.

* * * * *